(12) United States Patent  (10) Patent No.: US 9,226,747 B2
Oren et al.  (45) Date of Patent: Jan. 5, 2016

(54) MEDICAL IMPLEMENT FOR MANIPULATING SUTURES PARTICULARLY USEFUL IN ARTHROSCOPIC SURGERY

(75) Inventors: Ran Oren, Kibbutz Gaaton-Doar-Na Oshrat (IL); Dan Moor, Kibbutz Gaaton-Doar-Na Oshrat (IL)

(73) Assignee: T.A.G. Medical Devices-Agriculture Cooperative Ltd., Kibbutz Gaaton (IL)

( * ) Notice: Subject to any disclaimer, the term of this patent is extended or adjusted under 35 U.S.C. 154(b) by 817 days.

(21) Appl. No.: 13/201,867

(22) PCT Filed: Feb. 17, 2010

(86) PCT No.: PCT/IL2010/000140
§ 371 (c)(1),
(2), (4) Date: Aug. 17, 2011

(87) PCT Pub. No.: WO2010/095131
PCT Pub. Date: Aug. 26, 2010

(65) Prior Publication Data
US 2011/0301622 A1 Dec. 8, 2011

Related U.S. Application Data

(60) Provisional application No. 61/152,980, filed on Feb. 17, 2009.

(51) Int. Cl.
*A61B 17/04* (2006.01)
*A61B 17/06* (2006.01)
(Continued)

(52) U.S. Cl.
CPC ....... *A61B 17/0483* (2013.01); *A61B 17/06109* (2013.01); *A61B 17/221* (2013.01); *A61B 17/32056* (2013.01)

(58) Field of Classification Search
CPC .......... A61B 17/0483; A61B 17/0485; A61B 17/32056
USPC .................................. 606/144, 148
See application file for complete search history.

(56) References Cited

U.S. PATENT DOCUMENTS 3,840,017 A * 10/1974 Violante ................. 606/146
5,562,683 A   10/1996 Chan
(Continued)

FOREIGN PATENT DOCUMENTS

DE   102005015687   10/2006
DE   202008011769   11/2008
(Continued)

OTHER PUBLICATIONS

Notice of Reasons for Rejection Dated Jan. 7, 2014 From the Japanese Patent Office Re. Application No. P2011-549732 and Its Translation Into English.
(Continued)

*Primary Examiner* — Gregory Anderson

(57) ABSTRACT

A medical implement particularly useful in arthroscopic sutures, includes: a handle having a proximal end configured for manual gripping by a user, a distal end, an internal passageway extending between the proximal end and the distal end, and an intermediate portion formed with a recess extending from the outer surface to the internal passageway. A shuttle is movable through the passageway and has an intermediate portion exposed within the recess for manipulation by a user gripping the handle, and a suture-receiving-element at its distal movable axially through the distal end of the handle. A roller is rotatably mounted to the handle to underlie the exposed portion of the shuttle such that, after a suture has been received by the suture-receiving-element of the shuttle, a user, gripping the handle, may manipulate the shuttle with respect to the distal end of the handle by thumb-pressing the exposed portion of the shuttle against the roller and rotating the roller.

16 Claims, 3 Drawing Sheets

(51) Int. Cl.
  *A61B 17/221* (2006.01)
  *A61B 17/3205* (2006.01)

(56) References Cited

U.S. PATENT DOCUMENTS

| | | | |
|---|---|---|---|
| 5,643,292 | A | 7/1997 | Hart |
| 5,681,331 | A | 10/1997 | De la Torre et al. |
| 5,755,728 | A | 5/1998 | Maki |
| 6,213,375 | B1* | 4/2001 | Rybicki ............... 228/41 |
| 6,511,488 | B1 | 1/2003 | Marshall et al. |
| 7,329,264 | B2 | 2/2008 | Merves |
| 7,704,262 | B2 | 4/2010 | Bellafiore et al. |
| 2004/0106935 | A1 | 6/2004 | Merves |
| 2005/0165416 | A1 | 7/2005 | Bojarski et al. |
| 2005/0283171 | A1 | 12/2005 | Bellafiore et al. |
| 2006/0069399 | A1 | 3/2006 | Weisel et al. |
| 2006/0178682 | A1 | 8/2006 | Boehlke |
| 2006/0229642 | A1 | 10/2006 | Oberlaender et al. |
| 2007/0179510 | A1 | 8/2007 | Stone |
| 2008/0221619 | A1 | 9/2008 | Spivey et al. |
| 2008/0275477 | A1 | 11/2008 | Sterrett et al. |
| 2010/0057111 | A1 | 3/2010 | Berberich et al. |
| 2011/0301621 | A1 | 12/2011 | Oren et al. |

FOREIGN PATENT DOCUMENTS

| | | |
|---|---|---|
| EP | 1709909 | 10/2006 |
| WO | WO 96/21394 | 7/1996 |
| WO | WO 2007/097994 | 8/2007 |
| WO | WO 2008/109625 | 9/2008 |
| WO | WO 2010/095112 | 8/2010 |
| WO | WO 2010/095131 | 8/2010 |

OTHER PUBLICATIONS

Translation of Notification of Office Action Dated Mar. 22, 2013 From the State Intellectual Property Office of the People's Republic of China Re. Application No. 201080007977.6.
Translation of Search Report Dated Mar. 22, 2013 From the State Intellectual Property Office of the People's Republic of China Re. Application No. 201080007977.6.
Office Action Dated May 2, 2013 From the Israel Patent Office Re. Application No. 214584 and Its Translation Into English.
Office Action Dated Oct. 10, 2013 From the Israel Patent Office Re. Application No. 214584 and Its Translation Into English.
Notification of Office Action Dated Jan. 20, 2014 From the State Intellectual Property Office of the People's Republic of China Re. Application No. 201080007976.1 and Its Translation Into English.
Office Action and Search Report Dated Mar. 22, 2013 From the State Intellectual Property Office of the People's Republic of China Re. Application No. 201080007977.6.
Translation of Notification of Office Action Dated May 23, 2013 From the State Intellectual Property Office of the People's Republic of China Re. Application No. 201080007976.1.
Translation of Search Report Dated May 23, 2013 From the State Intellectual Property Office of the People's Republic of China Re. Application No. 201080007976.1.
Official Action Dated Jun. 26, 2013 From the US Patent and Trademark Office Re. U.S. Appl. No. 13/201,864.
International Search Report and the Written Opinion Dated Jul. 7, 2010 From the International Searching Authority Re.: Application No. PCT/IL2010/000141.
International Search Report and the Written Opinion Dated May 12, 2010 From the International Searching Authority Re.: Application No. PCT/IL2010/000140.
Official Action Dated Dec. 5, 2012 From the US Patent and Trademark Office Re. U.S. Appl. No. 13/201,864.
International Preliminary Report on Patentability Dated Sep. 1, 2011 From the International Bureau of WIPO Re. Application No. PCT/IL2010/000140.
International Preliminary Report on Patentability Dated Sep. 1, 2011 From the International Bureau of WIPO Re. Application No. PCT/IL2010/000141.
Applicant-Initiated Interview Summary Dated Oct. 4, 2013 From the US Patent and Trademark Office Re. U.S. Appl. No. 13/201,864.
Notice of Reasons for Rejection Dated Nov. 12, 2013 From the Japanese Patent Office Re. Application No. 2011-549733 and Its Translation Into English.
Advisory Action Before the Filing of an Appeal Brief Dated Sep. 11, 2013 From the US Patent and Trademark Office Re. U.S. Appl. No. 13/201,864.
Communication Under Rule 71(3) EPC Dated Aug. 18, 2014 From the European Patent Office Re. Application No. 10710455.6.
Patent Examination Report Dated Jun. 18, 2014 From the Australian Government, IP Australia Re. Application No. 2010215109.
Notice of Reasons for Rejection Dated Sep. 30, 2014 From the Japanese Patent Office Re. Application No. P2011-549732 and Its Translation Into English.
Office Action Dated Dec. 15, 2014 From the Israel Patent Office Re. Application No. 214233.
Requisition by the Examiner and the Examination Search Report Dated Feb. 17, 2015 From the Canadian Intellectual Property Office Re. Application No. 2,751,735.
Translation Dated Jan. 15, 2015 of Office Action Dated Dec. 15, 2014 From the Israel Patent Office Re. Application No. 214233.

\* cited by examiner

MEDICAL IMPLEMENT FOR MANIPULATING SUTURES PARTICULARLY USEFUL IN ARTHROSCOPIC SURGERY

RELATED APPLICATIONS

This application is a National Phase of PCT Patent Application No. PCT/IL2010/000140 having International filing date of Feb. 17, 2010, which claims the benefit of priority of U.S. Provisional Patent Application No. 61/152,980 filed on Feb. 17, 2009. The contents of the above applications are all incorporated herein by reference.

FIELD AND BACKGROUND OF THE INVENTION

The present invention relates to a medical implement for manipulating sutures. The invention is particularly useful in arthroscopic surgery or other minimally invasive surgery, and is therefore described below with respect to such an application.

In minimally invasive surgery, such as arthroscopic surgery, all operations must be performed through a narrow opening, the size of which limits the size of the instruments used and the free space available to manipulate them. Small-size cutting, grasping, debriding and stitching instruments, capable of operating through small portals, have been developed for this purpose.

Internal suturing is necessary in many arthroscopic procedures, in order to close wounds, repair tissue tears, or to reattach tissue which becomes detached from its normal position. A strand of suture must be applied to the location to be sutured, and the suture must then be passed through a layer of tissue and retrieved from the exit side. In other cases sutures attached to an anchoring element must be captured and passed through tissue.

Many suture passing and stitching devices are available to the arthroscopist. For example, U.S. Pat. No. 5,499,991, U.S. Pat. No. 5,222,977, as well as catalogs of Linvatec-Concept Inc., Arthrex Inc., DePuy Mitek Inc. and others describe and advertise such devices. All these devices are limited either to a part of the functions necessary, or in directions of approach, or in maneuverability in limited space.

OBJECTS AND BRIEF SUMMARY OF THE INVENTION

An object of the present invention is to provide a medical implement particularly useful in arthroscopic surgery and having advantages in one or more of the above respects.

According to a broad aspect of the present invention, there is provided a medical implement particularly useful in arthroscopic sutures, comprising:

a handle having a proximal end configured for manual gripping by a user, a distal end, an internal passageway extending between the proximal end and the distal end, and an intermediate portion formed with a recess extending from the outer surface to the internal passageway;

a shuttle movable through the passageway and having an exposed intermediate portion within the recess for manipulation by a user gripping the handle, and a suture-receiving-element at its distal movable axially through the distal end of the handle;

and a roller rotatably mounted to the handle underlying the exposed intermediate portion of the shuttle such that, after a suture has been received by the suture-receiving-element of the shuttle, a user, gripping the handle, may manipulate the shuttle with respect to the distal end of the handle by thumb-pressing the exposed portion of the shuttle against the roller and rotating the roller.

In the preferred embodiment of the invention described below, the implement further comprises a shaft having a proximal end joined to the distal end of the handle, a distal end formed with a pointed tip for piercing tissue, and a passageway from its proximal end to its distal end for receiving the movable shuttle.

According to further features in the described preferred embodiment, the shuttle includes a long flexible wire having a proximal end extending outwardly of the proximal end of the handle, and a distal end formed with a loop defining the suture-receiving-element. The long flexible wire of the shuttle includes two strands formed at its distal end with the loop.

According to still further features in the described preferred embodiment, the handle is further formed with a slot having a longitudinally-extending section extending along one side of the handle and terminating in a transversely-extending section adjacent to the recess in the handle and spaced therefore in the proximal direction; the slot communicating with the internal passageway through the handle to permit side-loading of the shuttle through the handle.

In addition, the transversely-extending section of the slot terminates in a proximally-extending notch effective to center the shuttle with respect to the handle, and therefore also with respect to the recess therein and to overlie the central area of the roller underlying the recess.

As will be described more particularly below, such a medical instrument is particularly useful in arthroscopic surgery wherein all operations must be performed through a narrow opening.

BRIEF DESCRIPTION OF THE DRAWINGS

The invention is herein described, by way of example only, with reference to the accompanying drawings, wherein.

Figure 1:
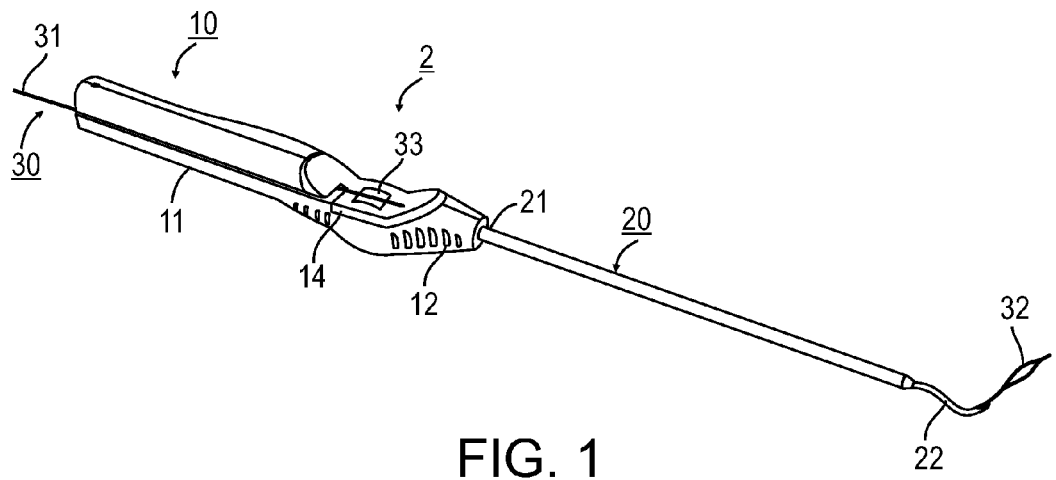
FIG. 1 is a perspective view of one preferred embodiment of a medical suture passing implement constructed according to the present invention for use in suturing within the shoulder.
Figure 2:
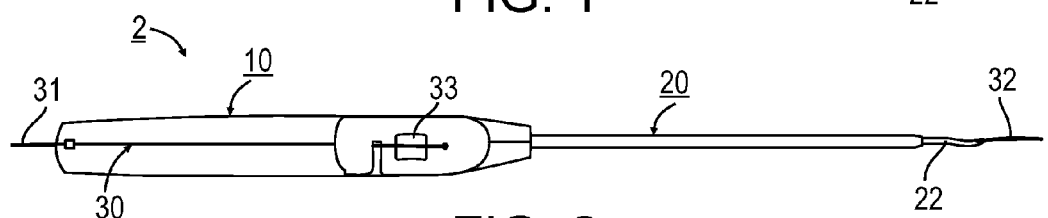
FIG. 2 is a top view of the implement of FIG. 1.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

Overall Construction

The medical implement illustrated in FIGS. 1-5 of the drawings, and therein generally designated 2, includes three main parts: a handle 10 having a proximal end 11 configured for manually grasping and a distal end 12; an elongated shaft 20 having a proximal end 21 joined to the distal end 12 of the handle, and a distal end formed with a pointed tip 22 for piercing tissue; and a long flexible wire 30 receivable within, and manually moveable through, an interior passageway 13 (FIG. 4) of the handle 10 and elongated shaft 20.

The long flexible wire 30 constitutes a shuttle for manipulating a suture, as will be disclosed more particularly below. It consists of two twisted strands having a proximal end 31 extending outwardly of the proximal end 11 of handle 10; a distal end twisted at its tip to form a loop 32 for receiving the suture to be passed through the tissue; and an intermediate portion 33 (FIG. 3) exposed for manual engagement by the thumb of user gripping the handle in order to extend or retract the distal loop 32.

Figure 3:
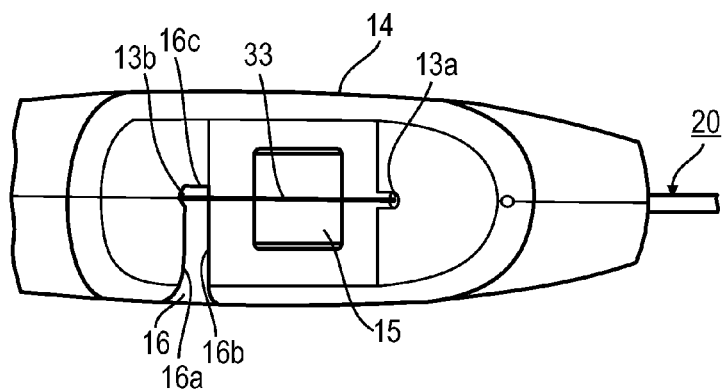
FIG. 3 is an enlarged fragmentary view of a portion of FIG. 2.
Figure 4:
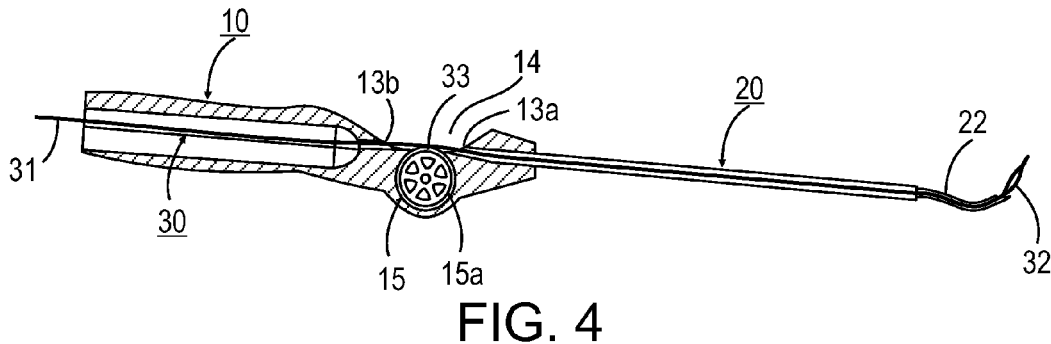
FIG. 4 is a sectional view along line V-V' in FIG. 2.

As shown particularly in FIGS. 3 and 4, handle 10 is formed, adjacent its distal end 12, with a recess 14 extending along the outer surface of the handle towards, but terminating short of, the distal end 12 of the handle. Recess 14 also extends inwardly from the outer surface to the passageway 13 through the handle receiving the long flexible wire 30 so as to expose the intermediate portion 33 of the wire to the thumb of the user grasping the handle.

In addition, the implement further includes a roller 15 rotatably mounted at 15a to the handle so as to underlie the exposed intermediate portion 33 of the long flexible wire 30 received within passageway 13 of the handle. Preferably, the outer surface of roller 15 is knurled or ribbed or is made of an elastomeric material, to enable the user, by pressing the exposed wire portion 33 against the roller, to rotate the roller in either direction in order to move the wire 30, particularly its distal loop 32, outwardly from the elongated shaft 20 to extend the distal loop, or inwardly into the elongated shaft to retract the distal loop.

As shown particularly in FIG. 3, handle 10 is further formed with a slot 16 having a longitudinally-extending section 16a extending along one side of the handle and terminating in a transversely-extending section 16b adjacent to recess 14 in the handle and spaced therefrom in the proximal direction. The longitudinally-extending section 16a of slot 16 extends from the proximal end 11 of handle 10 to the transversely-extending section 16b at the proximal side of recess 14. Slot 16 communicates with the interior passageway 13 of handle 10 so as to permit side loading of the long flexible wire 30 through the handle and through the elongated shaft 20. The transversely-extending section 16b of slot 16 terminates in a proximally-extending notch 16c effective to center wire 30 with respect to the handle, and therefore also with respect to its recess 14 and to overlie the central area of roller 15 underlying the recess.

It will thus be seen that the proximal side of notch 15c communicates with the portion of internal passageway 13, between the transverse slot section 16b and the distal end of the handle, via an opening 13a at the proximal end of the notch. It will also be seen that the distal side of recess 14 communicates with the portion of passageway 13 between the recess and the distal end of the handle via an opening 13b.

Use and Operation

The manner of loading the implement with the long flexible wire 30, and of using the implement for passing sutures through tissue, will now be described, particularly with reference to FIGS. 7a-7c.

Figure 7A:
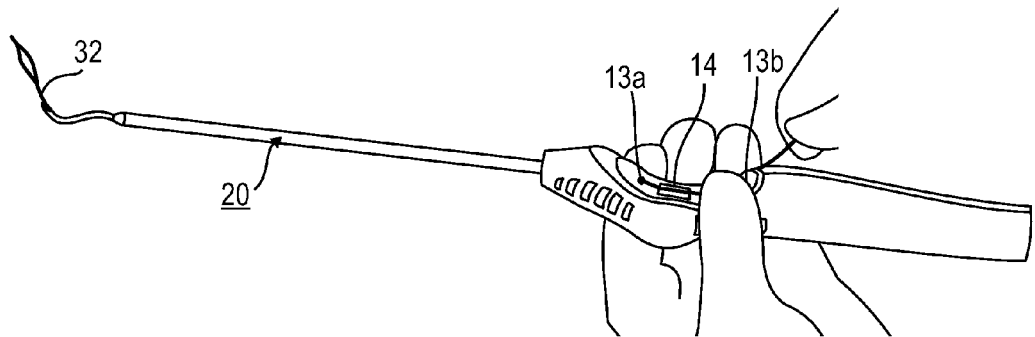
FIGS. 7A-7D illustrate the method of loading the implement with a long flexible wire formed at its distal end with a loop for receiving a suture to be passed through tissue.
Figure 7B:
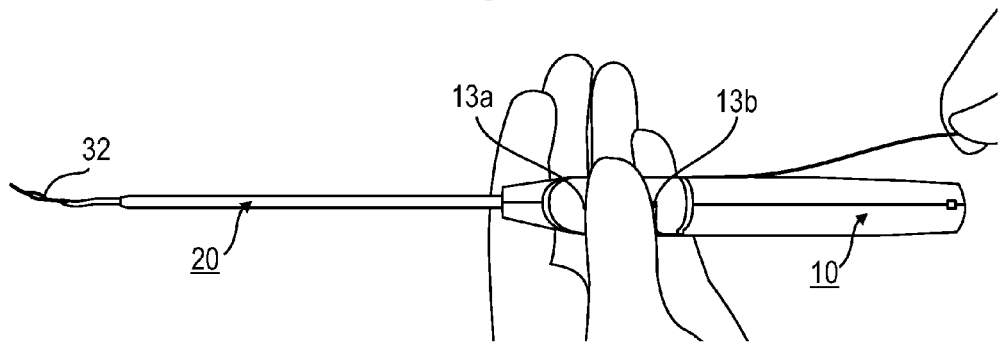
Figure 7C:
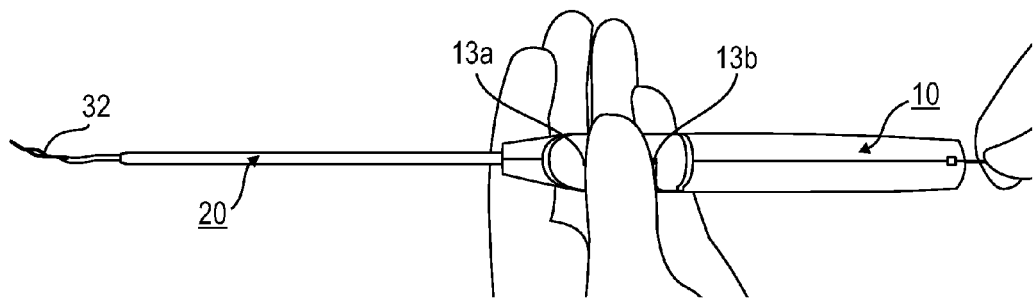

Thus, as shown in FIG. 7a, the loop 32 at the distal end of the flexible wire 30 is inserted into opening 13b of passageway 13 at the distal side of the recess 14 to overlie the roller 15. The wire is then manually advanced distally through the passageway, and through the elongated shaft 20, by thumb pressing the intermediate portion 33 of the wire against roller 15, while moving the thumb in order to advance the wire within the hollow shaft 20. The user then, with one hand, presses the wire against roller 15 in order to temporarily immobilize the wire, while the other hand side-loads the proximal end of the wire into the section of the interior passageway 13 between slot section 16b and the proximal end of the handle. This is done by passing the proximal end of the wire through the longitudinal slot section 16a into the transversely-extending slot section 16b, and then into notch 16c of the slot terminating in opening 13b. The notch centers the wire with respect to the handle recess 14 and the roller 15 underlying the recess (FIG. 7b), while the proximal end of the wire extends through the proximal end of the passageway 13 in the handle 10 (FIG. 7c).

Figure 7D:
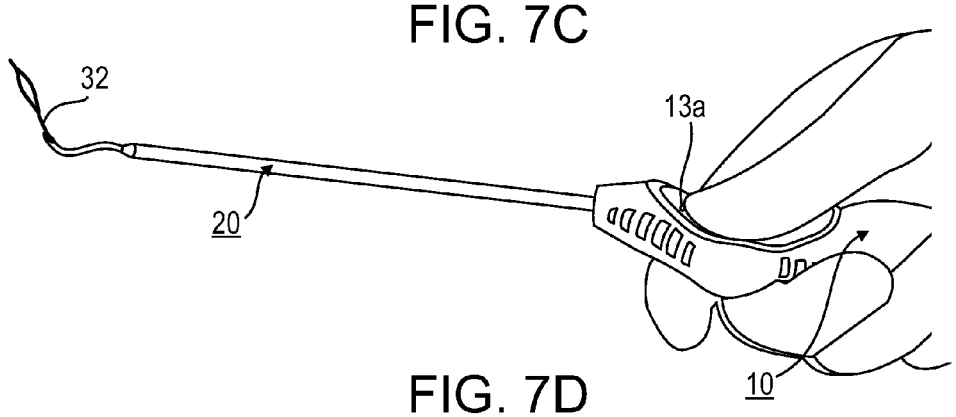

The implement is thus loaded (FIG. 7d) such that thumb-pressing portion 33 of the wire, exposed in recess 14, and moving the thumb forwardly will project the distal loop 32 of the wire outwardly of elongated shaft 20, while moving the thumb in the opposite direction will retract the loop within the elongated shaft.

Figure 5:
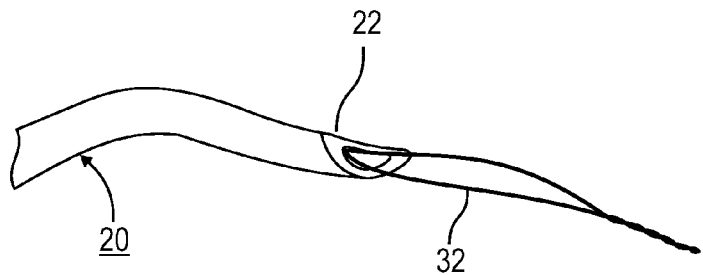
FIG. 5 is an enlarged view of the distal end of the medical implement of FIG. 1, and particularly the wire loop projecting from the tip at the distal end.
Figure 6A:
FIGS. 6A, 6B, 6C, 6D, 6E, 6F and 6G are alternative configurations of the distal tip of the implement shown in FIG. 4.
Figure 6B:
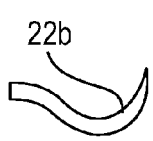
Figure 6C:
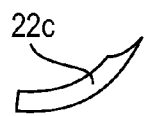
Figure 6D:
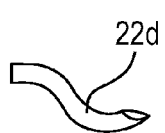
Figure 6E:
Figure 6F:
Figure 6G:

When the illustrated implement is used for passing a suture through tissue, the implement is inserted through a portal at the surgical site; and the tissue to be sutured is then pierced with the sharp distal tip 22 (FIG. 5) of the elongated shaft 20. The wire is then advanced by rotating roller 15, while the intermediate wire portion 33 is pressed against the outer surface of the roller, until loop 32 of the distal tip protrudes outwardly of the sharpened tip 22 of shaft 20, as shown in FIG. 5.

A suture manipulating device may then be used to thread the suture into the loop 32. When this is done, the wire is then retracted into the shaft 20 until the suture is held against the distal end of the shaft. The distal end of shaft 20, with the suture held to it, is then passed through the tissue.

The implement, with the suture held to the distal tip of the shaft 20, may then be passed through the portal to the outside, and the suture freed from the loop for knotting. Alternatively, once the suture is passed through the tissue, the suture may be released from the implement, by releasing the pressure applied against portion 14 of the wire, to remove the implement from the suture, if so convenient to the surgeon.

Some Variations

FIGS. 6a-6g illustrate various helical, corkscrew, or other curved arrangements, shown at 22a-22g respectively, that may be formed at the distal end of the elongated shaft 20 in order to facilitate piercing of tissue at any relative orientation to the elongated shaft when inserted via the portal opening into the patient's body. Such variations in the distal sharpened tip of the elongated shaft may be provided in a set of implements constructed with such distal tips, or may be included as attachments to the distal end of the elongated shaft.

While the invention has been described with respect to one preferred embodiment, it will be appreciated that this is set forth merely for purposes of example, and that many other variations, modifications and applications of the invention may be made.

What is claimed is:

1. A medical implement particularly useful in arthroscopic sutures, comprising:
    a handle having a proximal end configured for manual gripping by a user, a distal end, an internal passageway extending between the proximal end and the distal end, and an intermediate portion formed with a recess extending from the outer surface to the internal passageway;
    a shuttle movable through the passageway and having an intermediate portion exposed within the recess for manipulation by a user gripping the handle, and a suture-receiving-element at its distal end movable axially through the distal end of the handle;
    and a roller rotatably mounted to the handle underlying the exposed intermediate portion of the shuttle such that thumb-pressing the exposed intermediate portion of the shuttle engages the shuttle against the roller, so that after a suture has been received by the suture-receiving-element of the shuttle, a user, gripping the handle, may manipulate the shuttle with respect to the distal end of the handle by thumb-pressing the exposed portion of the shuttle against the roller, said shuttle held to a surface of said roller in response to being pressed by the thumb, and moving the thumb to advance or retract said shuttle.

2. The implement according to claim 1, wherein the implement further comprises a shaft having a proximal end joined to the distal end of the handle, a distal end formed with a pointed tip for piercing tissue, and a passageway from its proximal end to its distal end for receiving the movable shuttle.

3. The implement according to claim 1, wherein the shuttle includes a long flexible wire having a proximal end extending outwardly of the proximal end of the handle, and a distal end formed with a loop defining the suture-receiving-element.

4. The implement according to claim 3, wherein the long flexible wire of the shuttle includes two strands formed at its distal end with the loop.

5. The implement according to claim 1, wherein the handle is further formed with a slot having a longitudinally-extending section extending along one side of the handle and terminating in a transversely-extending section adjacent to the recess in the handle and spaced therefore in the proximal direction; the slot communicating with the internal passageway through the handle to permit side-loading of the shuttle through the handle.

6. The implement according to claim 5, wherein the transversely-extending section of the slot terminates in a proximally-extending notch effective to center the shuttle with respect to the handle, and therefore also with respect to the recess therein and to overlie the central area of the roller underlying the recess.

7. The implement according to claim 1, wherein the implement further comprises a shaft having a proximal end joined to the distal end of the handle, a distal end formed with a pointed tip for piercing tissue, and a passageway from its proximal end to its distal end for receiving the movable shuttle;
    and wherein the shuttle includes a long flexible wire having a proximal end extending outwardly of the proximal end of the handle, and a distal end formed with a loop defining the suture-receiving-element extending outwardly of the distal end of the shaft.

8. The implement according to claim 7, wherein the long flexible wire of the shuttle includes two strands formed at its distal end with the loop.

9. The implement according to claim 7, wherein the handle is further formed with a slot having a longitudinally-extending section extending along one side of the handle and terminating in a transversely-extending section adjacent to the recess in the handle and spaced therefore in the proximal direction; the slot communicating with the internal passageway through the handle to permit side-loading of the shuttle through the handle and the shaft.

10. The implement according to claim 9, wherein the transversely-extending section of the slot terminates in a proximally-extending notch effective to center the shuttle with respect to the handle, and therefore also with respect to the recess therein and to overlie the central area of the roller underlying the recess.

11. The implement according to claim 1, wherein the implement further comprises a shaft having a proximal end joined to the distal end of the handle, a distal end formed with a pointed tip for piercing tissue, and a passageway from its proximal end to its distal end for receiving the movable shuttle;
    and wherein the handle is further formed with a slot having a longitudinally-extending section extending along one side of the handle and terminating in a transversely-extending section adjacent to the recess in the handle and spaced therefore in the proximal direction; the slot communicating with the internal passageway through the handle to permit side-loading of the shuttle through the handle.

12. The implement according to claim 11, wherein the transversely-extending section of the slot terminates in a proximally-extending notch effective to center the shuttle with respect to the handle, and therefore also with respect to the recess therein and to overlie the central area of the roller underlying the recess.

13. The implement according to claim 1, wherein the shuttle includes a long flexible wire having a proximal end extending outwardly of the proximal end of the handle, and a distal end formed with a loop defining the suture-receiving-element;
    and wherein the handle is further formed with a slot having a longitudinally-extending section extending along one side of the handle and terminating in a transversely-extending section adjacent to the recess in the handle and spaced therefore in the proximal direction; the slot communicating with the internal passageway through the handle to permit side-loading of the shuttle through the handle.

14. The implement according to claim 13, wherein the transversely-extending section of the slot terminates in a proximally-extending notch effective to center the shuttle with respect to the handle, and therefore also with respect to the recess therein and to overlie the central area of the roller underlying the recess.

15. The implement according to claim 13, wherein the long flexible wire of the shuttle includes two strands formed at its distal end with the loop.

16. A method of manipulating a shuttle, comprising:
    loading a shuttle comprising a suture receiving element at its distal end onto an internal passageway extending between the proximal and distal ends of a handle of a medical implement, the medical implement further comprising a roller rotatably mounted to the handle at a recess in an intermediate portion of the handle extending from the outer surface of the handle to the internal passageway, wherein the placement of the loaded shuttle is such that an intermediate portion of said shuttle overlies said roller, and said intermediate portion of said shuttle is exposed to a user;

thumb-pressing said exposed intermediate portion of said shuttle against said roller to engages said shuttle against a surface of said roller; and moving the thumb to advance or retract at least said suture-receiving element of said shuttle from a distal end of said passage.

\* \* \* \* \*